United States Patent [19]

Lamboo

[11] Patent Number: 4,591,958
[45] Date of Patent: May 27, 1986

[54] ULTRAVIOLET IRRADIATION PANEL

[75] Inventor: Theodorus F. Lamboo, Roosendaal, Netherlands

[73] Assignee: U.S. Philips Corporation, New York, N.Y.

[21] Appl. No.: 569,688

[22] Filed: Jan. 10, 1984

[30] Foreign Application Priority Data

Jan. 13, 1983 [NL] Netherlands ............... 8300115

[51] Int. Cl.⁴ ............................................. H01J 61/35
[52] U.S. Cl. ................... 362/219; 362/241; 250/504 R
[58] Field of Search .............. 362/219, 224, 225, 230, 362/241, 263, 255, 240, 296, 227; 250/494.1, 504 R

[56] References Cited

U.S. PATENT DOCUMENTS

| 2,247,409 | 7/1941 | Roper | 250/504 |
|---|---|---|---|
| 2,660,925 | 12/1953 | Turner | 362/296 |
| 3,987,331 | 10/1976 | Schreurs | 313/486 |
| 4,287,554 | 9/1981 | Wolff | 362/241 |
| 4,469,951 | 9/1984 | Coco | 250/504 R |

FOREIGN PATENT DOCUMENTS

| 2707908 | 8/1978 | Fed. Rep. of Germany | 250/494.1 |
| 2030694 | 4/1980 | United Kingdom | 250/494.1 |

Primary Examiner—Carl Stuart Miller
Attorney, Agent, or Firm—David R. Treacy

[57] ABSTRACT

A housing having a front wall which is transparent to ultraviolet radiation, and an array of low-pressure mercury vapor discharge lamps arranged parallel to each other. At least the back facing half of each lamp is coated with an ultraviolet reflecting layer, and the lamps are spaced from each other a distance of less than one-fifth their outside diameters, so that ultraviolet radiation from the panel is maximized.

10 Claims, 3 Drawing Figures

ULTRAVIOLET IRRADIATION PANEL

BACKGROUND OF THE INVENTION

The invention relates to an irradiation device for emitting ultraviolet radiation, which device comprises a housing in which are arranged a number of parallel extending tubular low-pressure mercury vapor discharge lamps which emit at least ultraviolet radiation having a wave-length of more than 315 nm during operation. The inner wall of each lamp is provided with an ultraviolet reflecting a layer extending over the length of the lamp, but only along part of the tube circumference. Such an irradiation device is known from the Dutch Patent Application No. 7710575 laid open for public inspection.

The aforementioned device is used for photochemical or photobiological applications, for example, in sun beds and solaria, in which the skin of a person situated on or near a transparent wall of the housing is exposed for some time to ultraviolet radiation, especially ultraviolet radiation having a wave-length of more than 315 nm (UV-A radiation).

In order to increase the radiation output of the device, according to the German Offenlegungsschrift No. 2804228, a gutter-shaped reflector is arranged behind each tubular lamp. For a further increase of the radiation output, the number of radiation lamps in the housing could be increased, but it has been found that the relative contribution of the reflectors to the radiation output then decreases strongly. It has further been found that, for example due to the poor ventilation, a comparatively small amount of cool air flows along the lamp walls and the operating temperature of the lamps readily increases to an excessively high value. The mercury pressure then increases to a value exceeding approximately $6 \times 10^{-3}$ Torr. At a vapour pressure exceeding $6 \times 10^{-3}$ Torr, the efficiency of the conversion of the electric energy supplied to a lamp into resonance radiation of mercury having a wave-length of 254 nm decreases. Additionally, the effectiveness of any ventilator, which is located in the housing of the known device, for example, for cooling purposes and which is often located under the reflectors, is low due to the presence of these reflectors.

The aforementioned Dutch Patent Application discloses an irradiation chamber comprising a system of vertically arranged fluorescent irradiation lamps, each provided with an inner reflecting layer surrounding an irradiation space. Further, reflectors are present on the upper and the lower side of the irradiation space. The lamps are also surrounded by a transparent protecting envelope. In this case, there is a risk that due to the low cooling the mercury vapor pressure in the lamp increases to an excessively high value and the radiation output is reduced. Due to the presence of the envelopes, the number of lamps to be used in the device is comparatively small. Moreover, there is a risk of reduction of the radiation output during operation, due to absorption of radiation by the envelope.

SUMMARY OF THE INVENTION

The invention has for its object to provide an ultraviolet irradiation device in which the radiation output is much greater than that of the known device, and in which the aforementioned disadvantages are obviated.

Therefore, according to the invention, an irradiation device of the kind mentioned in the opening paragraph is characterized in that the longitudinal axes of two adjacent tubular low-pressure mercury vapour discharge lamps are located at a relative distance of from 1.01 D to 1.20 D, where D is the outer diameter of the tubular lamps.

An irradiation device according to the invention has the advantage that a larger number of lamps can be used without the dimensions of the housing being varied. It has been found that due to the absence of an external envelope surrounding a lamp the operating temperature of the lamps can be readily stabilized, for example by means of a blower present in the housing, at a value at which the aforementioned conversion efficiency is an optimum. The absence of the envelope or the external reflector moreover has a cost-saving effect. The reflecting layer in a lamp extends over a part of the circumference of the inner wall of 180° to 240° to provide a radiation exit window (which is free from reflecting material) which is so proportioned that, in conjunction with the aforementioned relative distance of the lamps, a very favourable radiation output of the irradiation device is obtained. The radiation output of the device per unit surface area of the radiation emanating surface is very high. It has been found that there is still sufficient room between the lamps for circulation of comparatively cool air. It has further been found that the efficiency of the lamps during their operation was substantially not adversely affected.

The reflecting layer in the lamps preferably comprises aluminum oxide. It has been found that for a long operating time such a reflecting material has a high reflection coefficient for the ultraviolet radiation having a wave-length of more than 315 nm, which is emitted by the lamps.

In the irradiation device according to the invention, low-pressure mercury vapour discharge lamps are preferably used, on which the luminescent layer which emits ultraviolet radiation is present along the whole circumference of the inner surface of the wall. The layer also extends over the aforementioned reflecting layer. The luminescent layer preferably comprises strontium tetraborate activated by bivalent europium emitting ultraviolet radiation in a narrow band (wave-length approximately 370 nm). In an alternative embodiment, the luminescent layer comprises barium disilicate activated by lead ($\lambda$ being approximately 350 nm).

The irradiation device according to the invention can be used as a couch-type sun panel, a suspended sunpanel or a wall-type sun panel. Comparatively long low-pressure discharge lamps (for example approximately 1.8 m) are then arranged in the housing. When used as a so-called face irradiator, however, the length of the lamps is comparatively small (for example approximately 0.60 m).

An embodiment of the invention will be described more fully with reference to the drawing.

DESCRIPTION OF THE PREFERRED EMBODIMENT

Figure 1:
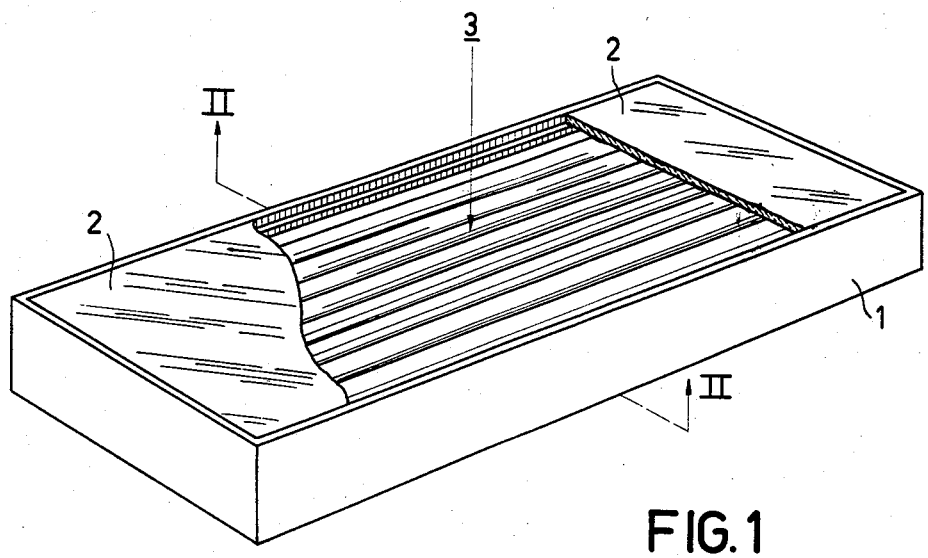
FIG. 1 is a perspective view of an irradiation device according to the invention.

The irradiation device for the emission of ultraviolet radiation shown in FIG. 1 constructed as a couch-type sun panel comprises a housing 1, which has a number of orthogonal walls. The upper or front side of the housing is provided with a plate 2, e.g. a glass or acrylic plate, which is transparent to ultraviolet radiation. The ultraviolet radiation emitted during the operation of the device has a wave-length of more than 315 nm (UV-A radiation) and is produced by ten tubular low-pressure mercury vapour discharge lamps 3 arranged in the housing. The lamps are arranged parallel to each other at a very small relative distance. In a practical embodiment, the outer diameter of each lamp is approximately 38 mm, while the distance between the longitudinal axes of two adjacent lamps (for example between 3b and 3c, see FIG. 2) is 41 mm (approximately 1.07 D). The inner surface of wall 3a of the glass discharge envelope of each lamp is provided with a layer 4 which reflects ultraviolet radiation and which extends throughout its length (see also FIG. 3). This reflecting layer consists of fine-grained aluminium oxide and is present over 180°–240° and preferably about 200° of the circumference of the tube. A radiation exit window 5 of approximately 160° is then left, which is free from the reflecting material.

Figure 3:
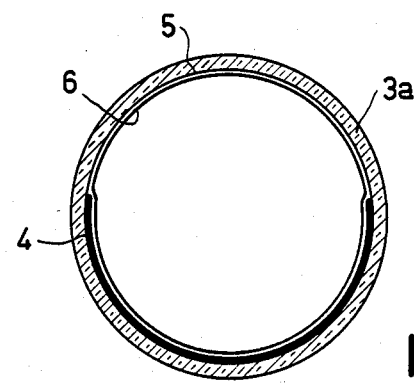
FIG. 3 is a cross-section of a low-pressure mercury vapour discharge lamp suitable to be used in an irradiation device of the kind shown in FIG. 1.

As is illustrated in FIG. 3, a luminescent layer 6 is present throughout the circumference of a lamp. This layer converts the resonance radiation produced in the mercury discharge and having a wave-lengtth of 254 nm into UV-A radiation. The luminescent layer is present both on the glass wall at the area of the said window and on the reflecting layer. In an embodiment, the luminescent layer comprises strontium tetra-borate activated by bivalent europium. The ultraviolet radiation emitted by this luminescent material has a wave-length of approximately 370 nm.

Figure 2:
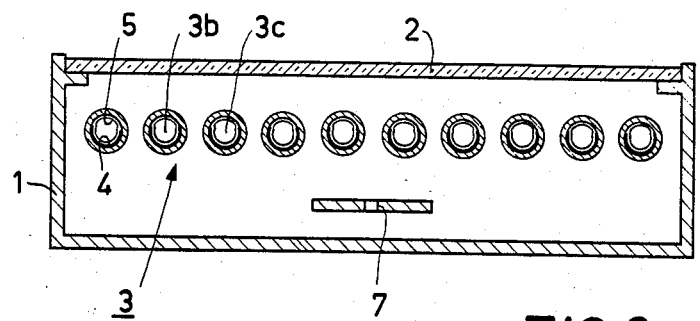
FIG. 2 is a cross-section of the irradiation device shown in FIG. 1 taken on the plane II—II.

As is shown in FIG. 2, the tubular discharge lamps 40 are located at a small relative distance.

In combination with the reflecting layer, an optimum radiation output is obtained, while the need for the use of an external reflector is avoided. The optimum operating temperature in the lamps is obtained by cooling the lamp walls, which is effected by blowing comparatively cool air along the lamp walls. This is achieved by means of a blower 7 which is present in the housing and is shown diagrammatically in FIG. 2.

In a practical embodiment, the housing has a length of approximately 2 m, a height of approximately 15 cm and a width of approximately 60 cm. The length of the tubular lamps is approximately 1.80 m (power approximately 85 W), and each lamp has an external diameter of 38 mm, the distance between the longitudinal axes of two adjacent lamps being approximately 41 mm so that the lamps are spaced apart a distance of approximately 3 mm). The inner wall surface of each lamp was provided with a layer of aluminum oxide which reflects ultraviolet radiation (over 200°) of the circumference and further with a luminescent layer comprising strontium borate activated by bivalent europium. It has been found that with the aforementioned dimensions of the housing ten lamps could be arranged, whereby 85% of the ultraviolet radiation emitted by the lamps is transmitted from the housing through the transparent plate 2.

What is claimed is:

1. An ultraviolet irradiation device, comprising:
   a housing having a front wall which is transparent to ultraviolet radiation,
   a plurality of straight, circular tubular low-pressure mercury vapor discharge lamps disposed within said housing, parallel to each other, each lamp having an inner wall having an ultraviolet reflecting layer extending over the length of the lamp, said layer extending along part of the circumference of the lamp,
   characterized in that said lamps are arranged in a planar array, spaced from each other such that the longitudinal axes of adjacent lamps are at a distance of from 1.01 to 1.20 times the outer diameter of the individual lamps, and
   the respective reflecting layers extend symmetrically across that portion of the circumference of each lamp which is toward the rear of said housing, over at least 180° and not more than 240° of the tube circumference.

2. A device as claimed in claim 1, characterized in that each reflecting layer extends over approximately 200° of each respective tube's circumference.

3. A device as claimed in claim 2, characterized in that said lamps are spaced with their longitudinal axes at a distance of approximately 1.07 times the lamp outer diameter.

4. A device as claimed in claim 3, characterized by comprising a blower arranged in the housing for blowing air along the walls of the lamps.

5. A device as claimed in claim 1, characterized in that said lamps are spaced with their longitudinal axes at a distance of approximately 1.07 times the lamp outer diameter.

6. A device as claimed in claim 5, characterized by comprising a blower arranged in the housing for blowing air along the walls of the lamps.

7. An ultraviolet irradiation device, comprising:
   a housing having a front wall which is transparent to ultraviolet radiation,
   a plurality of straight, circular tubular low-pressure mercury vapor discharge lamps disposed within said housing, parallel to each other, each lamp having an inner wall having an ultraviolet reflecting layer extending over the length of the lamp, said layer extending along part of the circumference of the lamp,
   characterized in that said lamps are arranged in a planar array, spaced from each other such that the longitudinal axes of adjacent lamps are at a distance of from 1.01 to 1.20 times the outer diameter of the individual lamps,
   each ultraviolet reflecting layer is a layer of fine-grained aluminum oxide particles, and
   the respective reflecting layers extend symmetrically across that portion of the circumference of each lamp which is toward the rear of said housing, over at least 180° and not more than 240° of the tube circumference.

8. A device as claimed in claim 7, characterized in that said reflecting layer extends over approximately 200° of each respective tube's circumference.

9. A device as claimed in claim 7, characterized in that said lamps are arranged such that there is a distance of approximately 3 mm between adjacent lamps.

10. A device as claimed in claim 7, characterized in that said lamps are spaced with their longitudinal axes at a distance of approximately 1.07 times the lamp outer diameter.

* * * * *